United States Patent
Bureau et al.

(10) Patent No.: US 9,783,619 B2
(45) Date of Patent: Oct. 10, 2017

(54) HYPOGLYCEMIC HYPER-BRANCHED MALTODEXTRINS

(71) Applicant: ROQUETTE FRERES, Lestrem (FR)

(72) Inventors: Stephanie Bureau, Essars (FR); Laetitia Guerin-Deremaux, Nieppe (FR); Bernard Pora, Hubei (CN)

(73) Assignee: Roquette Frères, Lestrem (FR)

(*) Notice: Subject to any disclaimer, the term of this patent is extended or adjusted under 35 U.S.C. 154(b) by 0 days.

(21) Appl. No.: 14/379,362

(22) PCT Filed: Feb. 27, 2013

(86) PCT No.: PCT/FR2013/050407
§ 371 (c)(1),
(2) Date: Aug. 18, 2014

(87) PCT Pub. No.: WO2013/128121
PCT Pub. Date: Sep. 6, 2013

(65) Prior Publication Data
US 2015/0025037 A1    Jan. 22, 2015

(30) Foreign Application Priority Data
Feb. 28, 2012 (FR) .................. 12 51810

(51) Int. Cl.
| | | |
|---|---|---|
| *A23L 1/30* | (2006.01) | |
| *A23L 1/307* | (2006.01) | |
| *C08B 30/18* | (2006.01) | |
| *C12P 19/04* | (2006.01) | |
| *C12P 19/20* | (2006.01) | |
| *A23L 29/30* | (2016.01) | |
| *A23L 33/10* | (2016.01) | |
| *A23L 33/20* | (2016.01) | |

(52) U.S. Cl.
CPC ............. *C08B 30/18* (2013.01); *A23L 29/30* (2016.08); *A23L 29/35* (2016.08); *A23L 33/10* (2016.08); *A23L 33/20* (2016.08); *C12P 19/04* (2013.01); *C12P 19/20* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,264,568 A | | 11/1993 | Yamada et al. |
| 5,620,873 A | * | 4/1997 | Ohkuma ............... A21D 2/186 435/101 |
| 6,630,586 B1 | | 10/2003 | Fouache et al. |
| 6,861,519 B2 | * | 3/2005 | Backer ................. A61M 1/287 162/1 |

FOREIGN PATENT DOCUMENTS

| | | | |
|---|---|---|---|
| EP | 0368451 A2 | 5/1990 | |
| EP | 0443789 A1 | 8/1991 | |
| EP | 0530111 A1 | 3/1993 | |
| EP | 0535627 A1 | 4/1993 | |
| EP | 0540421 A1 | 5/1993 | |
| EP | 1006128 A1 | 6/2000 | |
| JP | 04135595 A | 5/1992 | |
| JP | 04237497 A | 8/1992 | |
| JP | 2011-130696 | * 7/2011 | ............. C12P 19/14 |
| WO | 2009075564 A1 | 6/2009 | |

OTHER PUBLICATIONS

Ohkuma, K., Wakabayashi, S. (2008) Chapter 44: Fibersol-2: A Soluble, Non-digestible, Starch-Derived Dietary Fibre. Advanced Dietary Fibre Technology, p. 509-523.*

Fibersol-2. Retrieved [online]. Retrieved on Apr. 21, 2016. Retrieved from the internet at <http://www.adm.com/en- us/products/documents/fibersol%20technical%20brochure.pdf>.*

Wangsakan, A., Chinachoti, P., McClements, D.J. (2003) Effect of Different Dextrose Equivalent of Maltodextrin on the Interactions with Anionic Surfactant in an Isothermal Titration Calorimetry Study. Journal of Agricultural and Food Chemistry, vol. 51, p. 7810-7814.*

Oberlerchner, Molecules 2015, 20, 10313-10341.*

International Search Report, dated Jun. 24, 2013, from corresponding PCT application.

Englyst et al., "Digestion of polysaccharides of potato in the small intestine of man", Am. J. Clin. Nutr., 1987, vol. 45, pp. 423-431.

Bertrand, G., "Assay of reducing sugars", Bulletin des Sciences Pharmacologiques, Scientific and Professional Journal, 1907, vol. 14, No. 1.

Hakomori, I., "A Rapid Permethylation of Glycolipid, and Polysaccharide Catalyzed by Methylsulfinyl Carbanion in Dimethyl Sulfoxide", Letters to the Editors, The Journal of Biochemistry, 1964, vol. 55, No. 2, pp. 205-208.

Lane et al., "Determination of Reducing Sugars by Means of Fehling's Solution With Methylene Blue as Internal Indicator", Journal of the Society of Chemical Industry, 1923, Trans. 32-36.

(Continued)

*Primary Examiner* — Layla Berry
(74) *Attorney, Agent, or Firm* — Blank Rome LLP

(57) ABSTRACT

Hyper-branched maltodextrins having a dextrose equivalent (DE) between at least 8 and at most 15 and a molecular weight or Mw between at least 1,700 and at most 3,000 daltons, characterized in that same have: a 1,6 glucoside bond content between at least 30 and at most 45%; a soluble indigestible fiber content, which is determined according to the AOAC No. 2001-03 method, between at least 75 and at most 100%; and a hypoglycemic capacity expressed according to a test A, which:—in vitro, results in an 80 to 90% reduction of the α-amylase hydrolysis of standard maltodextrins, and—in situ, by a 30 to 45% reduction in the intestinal digestive activity of standard maltodextrins.

8 Claims, No Drawings

(56) References Cited

OTHER PUBLICATIONS

Livesey et al., "Interventions to lower the glycemic response to carbohydrate foods with a low-viscosity fiber (resistant maltodextrin): meta-analysis of randomized controlled trials", Am. J. Clin. Nutr., 2009, vol. 89, pp. 114-125.
Definition of Maltodextrins, Monograph Specifications of the Food Chemical Codex, CAS: [9050-36-6], pp. 239-240.

\* cited by examiner

HYPOGLYCEMIC HYPER-BRANCHED MALTODEXTRINS

The invention relates to novel hyper-branched maltodextrins of low molecular weight, i.e. having a dextrose equivalent (DE) between 8 and 15 and a molecular weight or Mw between 1700 and 3000 daltons, characterized by their particular 1→6 glucosidic bond content, their soluble indigestible fiber content, and especially their notable hypoglycemic properties.

More particularly, these novel hyper-branched maltodextrins have a 1→6 glucosidic bond content between 30% and 45%, a soluble indigestible fiber content between 75% and 100% (according to AOAC method No. 2001-03) and notable hypoglycemic properties, that they reflect, both in vitro and in situ, through a protective effect with respect to the digestion of standard maltodextrins.

For the purposes of the invention, "standard maltodextrins" are defined as purified and concentrated mixtures of glucose and of glucose polymers which are essentially α-1,4-bonded with only 4% to 5% of α-1,6 glucosidic bonds, which have varied molecular weights, which are completely soluble in water and which have a weak reducing power.

These standard maltodextrins are conventionally produced by acid hydrolysis or enzymatic hydrolysis of cereal starch or of tuberous plant starch. The classification of standard maltodextrins is based mainly on the measurement of their reducing power, conventionally expressed by the notion of Dextrose Equivalent or D.E. With regard to this particular point, the definition of maltodextrins reproduced in the *Monograph Specifications of the Food Chemical Codex* specifies that the D.E. value should not exceed 20.

For the purposes of the invention, the "protective effect" expressed by the hyper-branched maltodextrins of the invention in comparison with standard maltodextrins results in their capacity, when mixed with standard maltodextrins:

in vitro, to reduce the α-amylase hydrolysis of said standard maltodextrins by 80% to 90%;
in situ, in the intestine, to reduce the intestinal digestive activity of these standard maltodextrins by 30% to 45%.

By acting on the digestion and absorption of carbohydrates, e.g. standard maltodextrins, the hyper-branched maltodextrins of the invention slow down and therefore reduce the increase in glycemia following a meal (postprandial), and also the secretion of insulin.

This action is therefore capable of helping diabetics improve the control of their glycemia.

The invention is thus directed toward compositions comprising such hyper-branched maltodextrins that can be used in numerous industrial applications, in particular in the food and pharmaceutical industries.

Finally, the invention relates to a process for producing said hyper-branched maltodextrins.

For some time, considerable interest has been focused on the definition of appropriate fiber-rich diets. It is in fact acknowledged that the intake of fibers in the diet has a beneficial effect on health.

Dietary fibers are often classified, according to their solubility, into insoluble and soluble fibers.

These two types of fibers are present in varying proportions in food products containing fibers. Oats, barley, fruits, fresh vegetables and dry vegetables (beans, lentils, chick peas) constitute good sources of soluble fibers, while whole cereals and wholegrain bread are rich in insoluble fibers.

Insoluble fibers, such as cellulose, resistant starches, corn fibers (spent grain) or soya fibers, have an essentially mechanical role in the gastrointestinal tract.

They are only very slightly fermented by the intestinal flora and contribute to reducing the intestinal transit time through a ballast effect.

Insoluble fibers thus contribute to preventing constipation by increasing the weight of the stools and by reducing the duration of intestinal transit.

Soluble fibers, such as pectin and inulin, which cannot be digested by the intestinal enzymes in humans, are fermented by the intestinal bacterial flora. This fermentation releases short-chain fatty acids in the colon, the effect of which is to reduce the pH thereof and, consequently, to limit the development of pathogenic bacteria and to stimulate the development of beneficial bacteria.

The short-chain fatty acids also constitute a significant source of energy for the cells of the colon and inhibit the growth and proliferation of cancerous cells of the intestine.

Many mechanisms are put forward in order to explain the beneficial effects of dietary fibers on carbohydrate and lipid metabolisms; they are not mutually exclusive.

The immediate effect of soluble fibers on postprandial glycemia has imposed a "mechanical" explanation for the action of dietary fibers:

extension of the gastric emptying time by increasing the viscosity of the food bolus;
effect of dilution and of barrier against the action of digestive enzymes on foods in the small intestine;
increase in the viscous layer which coats the small intestine, thus slowing down nutrient absorption time;
spreading out of nutrient absorption through an increase in the time from the mouth to the intestine.

The first studies, which date back to the end of the 1970s, showed that giving diabetic subjects a carbohydrate- and fiber-rich diet improved glycemic balance and reduced their insulin needs, which went against the dietetic and nutritional trends of the time.

The short-term effects of dietary fibers on postprandial glycemia and insulinemia are widely documented and coherent: they affect the postprandial elevation of blood glucose level in insulin-treated, non-insulin-dependent and glucose-intolerant diabetic subjects and in healthy subjects. This effect is all the clearer when it is a question of soluble fibers.

It therefore results from the numerous studies that there is a relationship between complex sugars (polysaccharides, starch) and good colon physiology.

The impact of these complex sugars on the control of glycemia has been studied via the fate of resistant starches, not digested in the small intestine, which are thus of great interest for the health of the colon.

The targets of their functional effects are normally the colonic flora which ferments them and for which they serve as specific and selective substrates, gastrointestinal physiology and in particular the functions performed by the large intestine, the immune system, mineral bioavailability and lipid metabolism.

What therefore stands out is that soluble fibers:
slow down gastric emptying;
provide early satiety;
reduce the speed of carbohydrate (and also lipid) absorption in the small intestine.

The compounds conventionally classified in soluble fibers are fructooligosaccharides and transgalactooligosaccharides, but also lactulose, isomaltooligosaccharides, soya-extracted oligosaccharides, xylooligosaccharides, etc.

For example, fructooligosaccharides (FOSs) are short-chain fructose-unit polymers which are not hydrolyzed in the small intestine in humans, but are degraded by the resident flora of the colon.

FOSs principally induce the growth of endogenous lactobacilli and bifidobacteria of the intestine in humans and animals.

Alongside these compounds predominantly extracted from plants are molecules derived from starch or from partial or total hydrolysis products thereof.

Polydextrose is, for example, synthesized by random polymerization of glucose in the presence of sorbitol and of an appropriate acid catalyst (such as citric acid) and at high temperature.

Polydextrose is widely used in the diet as a filler and as a low-calorie ingredient. Polydextrose is neither digested nor absorbed in the small intestine and a considerable proportion is found in the feces.

Polydextrose is often combined with FOSs, since it would thus promote the consumption of lactic acid by specific flora, counterbalancing the overproduction thereof induced by FOSs.

However, also known in the prior art are a certain number of technologies which have been developed in order to treat starch so as to confer on it properties of dietary fibers, and thus to obtain resistant starches (Englyst and Cummings in *American Journal of Clinical Nutrition* in 1987, volume 45 pp. 423-431).

A starch is thus conventionally treated with a food acid at high temperature. This heat treatment will then generate starch derivatives of pyrodextrin, white dextrin or yellow dextrin type, depending on the amount of acid, on the water content of the starches, and on the temperature ranges used, these starch derivatives being resistant to digestion and to absorption in the small intestine in humans.

Indeed, while standard digestible maltodextrins and starches have only glucosidic bonds of $\alpha$-1,4 and $\alpha$-1,6 type, the heat treatment under acidic conditions and with a low water content will produce atypical bonds of 1,2 and 1,3 type (in alpha or beta anomerisms) which are not hydrolyzed by human digestive enzymes.

These physical treatments are often supplemented with enzymatic treatments in order to reinforce the dietary fiber nature of the resulting starch derivatives. Patents EP 368 451 and U.S. Pat. No. 5,264,568, for example, thus describe a process for preparing pyrodextrins, the dietary fiber characteristics of which are reinforced through the action of an $\alpha$-amylase or of several $\alpha$-amylases successively on a dextrin or on a polydextrin in solution at high temperature.

Patent EP 530 111 describes indigestible dextrins obtained by extrusion of a dehydrated acidified corn starch under specific conditions. This treatment can be supplemented with the action of a thermoresistant $\alpha$-amylase.

The applicant company has itself also described, in its patent application EP 1 006 128, "branched maltodextrins" having between 15% and 35% of 1,6 glucosidic bonds, a reducing sugar content of less than 20%, a polydispersity index of less than 5 and a number-average molecular weight Mn at most equal to 4500 g/mol.

These branched maltodextrins are especially indigestible in nature, the consequence of which is to reduce their calorific value by preventing their assimilation in the small intestine, and they therefore constitute a source of indigestible fibers.

It should be noted that fibers can be assayed according to various AOAC methods. By way of example, mention may be made of AOAC methods 997.08 and 999.03 for fructans, FOSs and inulin, AOAC method 2000.11 for polydextrose, AOAC method 2001.03 for assaying fibers contained in branched maltodextrins or AOAC method 2001.02 for GOSs and also soluble oligosaccharides originating from oleaginous plants or from protein-producing plants.

All these complex sugars have an impact on glycemia through their own nature which makes them indigestible, but fermentable by the beneficial bacteria of the colon, thus contributing to the integrity of the intestinal barrier.

Those skilled in the art in the field under consideration therefore use this range of products for their intrinsic properties.

This indigestible nature has thus been developed, for example, in patent EP 443 789 as a means for offering a food composition which regulates glycemia by lowering insulin secretion without impacting blood glucose level.

However, few studies have been undertaken in order to provide low-molecular-weight compounds which have intrinsically indigestible properties and which are capable of acting, in addition, specifically as barrier agents against the action of digestive enzymes on foods, even though, as in the studies by Livesey, G and Tagami, H, published in *Am. J. Clin. Nutr.*, 2009, 89, 114-25, one of the 6 mechanisms mentioned entirely generally as capable of explaining the effect of resistant maltodextrins on postprandial glycemia may be an enzymatic inhibition.

It results from all the aforementioned that, to the applicant company's knowledge, there are no low-molecular-weight, highly branched polysaccharides which have such hypoglycemic effects by reduction of carbohydrate digestion.

The applicant company has, to its credit, devised and produced, at the cost of a considerable amount of research, novel hyper-branched maltodextrins which specifically have this barrier effect.

The hyper-branched maltodextrins in accordance with the invention constitute a new family in the sense that it is clearly different than those of the prior art, including of the other low-molecular-weight branched maltodextrins that the applicant company has already proposed and described in its own prior patent applications.

For the purposes of the invention, the term "branched maltodextrins" is intended to mean the maltodextrins described in patent EP 1 006 128, of which the applicant company is the proprietor.

More particularly, the hyper-branched maltodextrins of the invention have a dextrose equivalent (DE) between at least 8 and at most 15 and a molecular weight or Mw between at least 1700 and at most 3000 daltons.

They are especially characterized by:
- a 1→6 glucosidic bond content between at least 30% and at most 45%,
- a soluble indigestible fiber content, determined according to AOAC method No. 2001-03, between at least 75% and at most 100%, and
- a hypoglycemic capacity, expressed according to a test A, which results:
  - in vitro, in an 80% to 90% reduction in the $\alpha$-amylase hydrolysis of standard maltodextrins,
  - in situ, in a 30% to 45% reduction in the intestinal digestive activity of standard maltodextrins.

A first family of products in accordance with the invention consists of hyper-branched maltodextrins having a DE between at least 8 and at most 12 and an Mw between at least 2500 and at most 3000 daltons, characterized by:

a 1→6 glucosidic bond content between at least 30% and at most 35%, a soluble indigestible fiber content, determined according to AOAC method No. 2001-03, between at least 75% and at most 80%.

A second family of products in accordance with the invention consists of hyper-branched maltodextrins having a DE between at least 12 and at most 15 and an Mw between at least 1700 and at most 2500 daltons, characterized by:

a 1→6 glucosidic bond content between at least 35% and at most 45%, a soluble indigestible fiber content, determined according to AOAC method No. 2001-03, between at least 80% and at most 100%.

The hyper-branched maltodextrins in accordance with the invention are first of all characterized by their DE and by their molecular weight.

As indicated above, the applicant company has developed and reported, in its patent application EP 1 006 128, "branched maltodextrins" having between 15% and 35% of 1,6-glucosidic bonds, a reducing sugar content of less than 20%, a polydispersity index of less than 5 and a number-average molecular weight Mn at most equal to 4500 g/mol.

The hyper-branched maltodextrins according to the invention, by virtue of their DE and their molecular weight, are similar to this family of branched maltodextrins.

The analytic parameters of the DE and of the molecular weight (or Mw) are determined by any method known, moreover, to those skilled in the art:

the method for determining the dextrose equivalent is, for example, the Lane-Eynon constant titration method (1923, *Determination of reducing sugars by means of Fehling's solution with methylene blue as internal indicator. J. Soc. Chem. Ind. Trans.* 32-36);

the Mw values are measured by size exclusion chromatography, based on the selective retention of the molecules of the solute as a function of their size, owing to their penetration or non-penetration into the pores of the stationary phase.

The hyper-branched maltodextrins of the invention thus have a DE limited to a value between 8 and 15, for a low molecular weight, between 1700 and 3000 daltons.

Moreover, and this is where the hyper-branched maltodextrins according to the invention differ from the branched maltodextrins of EP 1 006 128, they have:

an overall higher 1→6 glucosidic bond content, of between 30% and 45%, a high soluble indigestible fiber content, of between 75% and 100% (according to AOAC method No. 2001-03) and especially notable hypoglycemic properties.

The determination of the 1→2, 1→3, 1→4 and 1→6 glucosidic bond content is carried out according to the conventional methylation technique described in Hakomori, S. 1964, *J. Biol. Chem*, 55, 205.

With regard to the hypoglycemic properties, they are determined by carrying out an enzymatic digestion test in vitro and in situ, making it possible to measure the capacity of the hyper-branched maltodextrins of the invention to reduce the digestion of standard maltodextrins.

In terms of its "in vitro" component, this test consists in measuring, over time, the amount of reducing sugars released by the action of pig pancreatic α-amylase on standard maltodextrins in the presence of the hyper-branched maltodextrins of the invention.

The procedure is the following:

in a 250 ml beaker, weigh out exactly 50.0 g of standard maltodextrins of the type of those sold by the applicant company under the brand name Glucidex 6, weigh out exactly 5.0 g of hyper-branched maltodextrins to be tested and introduce them into the beaker, solubilize with 150 ml of demineralized water, correct the pH to the value of 5, if necessary, transfer into a 250 ml volumetric flask, rinse the beaker with a little water and adjust the flask to 250 ml with demineralized water, transfer into a 500 ml Erlenmeyer flask, place in an incubator at 37° C., add 25 mg of pig pancreatic α-amylase sold by Sigma under the reference A3176 (Type VI-B, ≥10 units/mg solid), remove 50 ml of solution at 3 hours, 6 hours and 24 hours of reaction, and inactivate for 10 minutes in a waterbath at 85° C., measure the reducing sugar content according to the method of Gabriel Bertrand ("Bulletin des sciences pharmacologiques" ["Bulletin of pharmacological sciences"], vol. 14, No. 1, January 1907).

The measurements are also carried out on the control (digestion of Glucidex® 6 alone with α-amylase) and the results of this in vitro test are expressed as % of α-amylase activity versus the control.

As will be exemplified hereinafter, the hyper-branched maltodextrins of the invention thus succeed in reducing by 80% to 90% the hydrolysis of Glucidex® 6 by pancreatic α-amylase.

By way of comparison, the branched maltodextrins developed by the applicant company in its patent EP 1 006 128 succeed only in reducing by 30% to 50% the hydrolysis of Glucidex® 6 by pancreatic α-amylase.

In terms of its "in situ" component, the test consists in carrying out a continuous intestinal perfusion in rats, so as to calculate the percentage of standard maltodextrin hydrolysis.

The procedure is the following:

The small intestine of a pre-anesthetized OFA rat from Sprague-Dawley, weighing approximately 300-350 g, is perfused at the level of the duodenum and of the ileum.

A closed circuit, in which a constant stream circulates, is produced.

The stream is provided by a peristaltic pump.

A solution of the product to be tested is injected into the circuit.

Polyethylene glycol (PEG) having a molecular weight in the region of 4000 is added to this solution. Said polyethylene glycol is used as a marker for the water movements in the intestine.

During the 2 hours of perfusion, the intestinal effluents are sampled.

After total acid hydrolysis, the amount of glucose assayed in the intestinal effluents, adjusted with respect to the PEG ratio (before and after perfusion) makes it possible to calculate the percentage hydrolysis of the product tested.

The protocol detailed is the following:

prepare a Ral® buffer solution, pH 7, at 4.68 g/l in physiological saline (0.15 M NaCl), prepare a solution of PEG 4000 at 1% in the buffer solution, prepare a solution to be perfused, of the product to be tested, at 10 g/l in the buffered PEG 4000 solution, give the animals no food for 24 hours, anesthetize the animal under isoflurane, perform a laparotomy,
perfuse the duodenum and the ileum (at approximately 5 cm from the cecum) using silicone tubing, ID 2 mm,
maintain the animal's body temperature on a hotplate set at 37° C.,
introduce 30 ml of solution to be perfused into this closed circuit,
start the peristaltic pump, set at 1 ml/min,
take samples at 30, 60 and 120 minutes.
The analyses are then carried out in the following way:
carry out the PEG assay on the initial perfusion solution (Po) and on the effluent (Pt),
assay the glucose in the effluent (FGt=Free Glucose at time t),
carry out a total acid hydrolysis on the initial sample of product and on the effluent,
assay the glucose (TGo: Total Glucose at time 0–TGt: Total Glucose at time t).
The formulae used are the following:
Branched Glucose (g/l)=BG=TGt−FGt
Branched Glucose adjusted with respect to the water movements in the intestinal lumen (BG'):

$$BG' = BG \times \frac{Po}{Pt}$$

percentage hydrolysis of the product tested:

$$\% \text{ hydrolysis} = \frac{(TGo - BG')}{TGo} \times 100$$

As will be exemplified hereinafter, the hyper-branched maltodextrins of the invention thus succeed in reducing by 30% to 45% the hydrolysis of Glucidex® 6 at the end of intestinal perfusion.

In order to prepare the hyper-branched maltodextrins in accordance with the invention, the succession of the following steps is carried out:
 a. a dehydrated acidified starch having a moisture content of less than 5%, preferably less than or equal to 4%, is prepared,
 b. the acidified starch thus dehydrated is treated in a thin-layer reactor at a temperature between 120 and 300° C., preferably between 150 and 200° C.,
 c. the resulting branched starch derivatives are collected, purified and preferably concentrated,
 d. a molecular fractionation of said branched starch derivatives is carried out so as to obtain a fraction having:
  i. an Mn between 250 and 400 g/mol,
  ii. a polydispersity index between 2 and 3,
  iii. a reducing sugar content between 20% and 30%,
  iv. a 1→6 glucosidic bond content between 30% and 35%,
 e. optionally, the resulting low-molecular-weight fraction is treated with an amyloglucosidase,
 f. the resulting solution is treated on a chromatographic column so as to exclude the oligomers having a degree of polymerization of 1 and 2,
 g. the resulting hyper-branched maltodextrins are recovered.

For the first four steps of the process in accordance with the invention (step a. to step d.), said steps resulting in the preparation of the low-molecular-weight fraction, any methods accessible to those skilled in the art can be used here.

However, the applicant company recommends using those described in its patent application EP 1 006 128, said steps being incorporated herein by way of reference (more particularly, those of Example 2 of EP 1 006 128 before the step of eliminating the glucose using glucose oxidase is carried out.

The low-molecular-weight fraction having:
 i. an Mn between 250 and 400 g/mol,
 ii. a polydispersity index between 2 and 3,
 iii. a reducing sugar content between 20% and 30%,
 iv. a 1→6 glucosidic bond content between 30% and 35%,
is then isolated at the level of the fourth plate of the chromatography column on Purolite C 145 macroporous cationic resin in potassium form, with a particle size of 250-350 µm, in 6-plate configuration.

The fifth step of the process (step e) in accordance with the invention, which is optional, consists in treating the resulting low-molecular-weight fraction with an amyloglucosidase.

The objective of this enzymatic treatment is to hydrolyze predominantly the linear structures of the resulting product (α 1→4 glucosidic bonds) so as to optimize the indigestible glucosidic bond content.

As will be exemplified, a treatment with an amyloglucosidase of Optidex L300A type (from the company Genencor) in a proportion of 0.5% on a dry basis, at a pH of 4.5, for from 5 to 10 h, preferably for 8 hours, is chosen.

The sixth step of the process (step f) in accordance with the invention consists in treating the resulting solution on a chromatographic column so as to exclude the oligomers having a degree of polymerization of 1 and 2.

This step can be carried out by any means known to those skilled in the art, for example by chromatography on Diaion UBR 35 K resin in sodium form, sold by the company Mitsubishi.

A weight yield of 40% makes it possible, as will be exemplified hereinafter, to limit the content of DP1+DP2 to a value <6% on a dry basis, preferably <0.5% on a dry basis.

The final step of the process in accordance with the invention consists, finally, in recovering the resulting hyper-branched maltodextrins.

The invention will be understood more clearly by means of the examples which follow, which are meant to be illustrative and nonlimiting.

EXAMPLE 1: PREPARATION OF THE HYPER-BRANCHED MALTODEXTRINS IN ACCORDANCE WITH THE INVENTION

Wheat starch is acidified with hydrochloric acid in a proportion of 19.6 meq H+/kg dry, and then dried to a residual moisture content of 4%.

This raw material is then introduced into a Buss PR 46 kneader maintained at a temperature of 180° C., at a flow rate of 20 kg/h, with a residence time of 5 seconds.

The reaction is rapidly stopped by spraying cold water at 15° C.

After purification by filtration, and discoloration on adsorbent resins and on cationic and anionic resins, the resulting branched starch derivatives are brought back to a solids content of 50%.

The product obtained is subjected to chromatography on Purolite C 145 macroporous strong cationic resin in potassium form, with a particle size of 250-350 µm, configured in 6 plates of 200 liters, maintained at 75° C.

The feed flow rates for the branched starch derivative syrup and for the elution water are fixed at 60 l/h and 400 l/h, at the level of the first and third plates, respectively. The choice of the second-plate and fourth-plate output flow rates conditions the obtaining of the high-molecular-weight and low-molecular-weight branched maltodextrin fractions.

The flow rate at the output of the fourth plate is fixed at 140 l/h. The fraction having an Mn of 400 g/mol is obtained with an adjustment of the chromatographic parameters fixing the yield at 30% (the yield being understood here to be the proportion of solids extracted from this high-molecular-weight fraction relative to the solids introduced into the chromatographic system).

The results of analysis of this low-molecular-weight fraction (product (A)), after chromatography, are grouped together in Table I below.

TABLE I

|  | Product (A) |
| --- | --- |
| DE | 30 |
| Mn (g/mol) | 400 |
| Mw (g/mol) | 1250 |
| Polydispersity index (Mw/Mn) | 3.1 |
| DP1 + DP2 (%) | 35 |
| 1, 2 bonds (%) | 11 |
| 1, 3 bonds (%) | 12 |
| 1, 4 bonds (%) | 44 |
| 1, 6 bonds (%) | 33 |
| AOAC fiber contents (%/dry) | 70.4 |

The exclusion of the DP1 and DP2 molecules is carried out by passing this low-molecular-weight fraction over a UBR 35 K chromatography column in $Na^+$ form.

The weight yield is estimated at 50%.

The resulting product is demineralized on cationic (C150 from Purolite) and anionic (Amberlite IRA 910 from Rohm & Haas) resins, and then optionally atomized.

The results of analysis of this hyper-branched maltodextrin in accordance with the invention (product (B)) are grouped together in Table II below.

TABLE II

|  | Product (B) |
| --- | --- |
| DE | 9 |
| Mn (g/mol) | 1595 |
| Mw (g/mol) | 2715 |
| Polydispersity index (Mw/Mn) | 1.7 |
| DP1 + DP2 (%) | <0.5 |
| 1, 2 bonds (%) | 10.3 |
| 1, 3 bonds (%) | 9.4 |
| 1, 4 bonds (%) | 49.6 |
| 1, 6 bonds (%) | 30.7 |
| AOAC fiber contents (%/dry) | 78 |

Exclusion of the DP1 and DP2 molecules is also carried out on the product (A) pretreated with amyloglucosidase (Optidex® L300A from Genencor; 0.5% on a dry basis, pH 4.5, at 60° C. for 8 hours).

The results of analysis of this hyper-branched maltodextrin in accordance with the invention (product C)) are grouped together in Table III below.

TABLE III

|  | Product (C) |
| --- | --- |
| DE | 14 |
| Mn (g/mol) | 865 |
| Mw (g/mol) | 2090 |
| Polydispersity index (Mw/Mn) | 2.4 |
| DP1 + DP2 (%) | 5.3 |
| 1, 2 bonds (%) | 9.2 |
| 1, 3 bonds (%) | 10.4 |
| 1, 4 bonds (%) | 37.6 |
| 1, 6 bonds (%) | 42.8 |
| AOAC fiber contents (%/dry) | 91.4 |

The treatment with amyloglucosidase followed by exclusion of the DP1 and DP2 molecules thus makes it possible to obtain the hyper-branched maltodextrins with a reinforced AOAC fiber content.

EXAMPLE 2: MEASUREMENT OF THE HYPOGLYCEMIC ROLE OF THE HYPER-BRANCHED MALTODEXTRINS OF THE INVENTION

The evaluation, in vitro, of the effect inhibiting α-amylase hydrolysis of standard maltodextrins and, in situ, of the inhibitory effect on intestinal digestion of standard maltodextrins was therefore carried out on the two products prepared according to the processes described in Example 1.

The result of the factor of inhibition of the pig pancreatic α-amylase activity on Glucidex® 6, in the presence of the hyper-branched maltodextrins (B) and (C) of Example 1, is given in the following table.

A branched maltodextrin in accordance with those prepared according to the teaching of patent EP 1 006 128 from the applicant company (sold by the applicant company under the brand name Nutriose® FB10), and commercial products, are also tested as controls.

By way of information, Nutriose® FB10 has the following characteristics:

DE: 10

Mw: 3996 daltons

1→6 glucosidic bond content: 33%.

With regard to polydextrose (sold under the brand name Litesse®), it has:

a DE: 8 an Mw: 1700 daltons a 1→6 glucosidic bond content: 42%

TABLE IV

| Product tested | Factor of inhibition of α-amylase activity on Glucidex® 6 |
| --- | --- |
| Product (B) | 91.9% |
| Product (C) | 81.1% |
| Nutriose® FB 10 | 49.6% |
| Litesse® | 29.4% |

With regard to the measurement of the inhibition of the intestinal digestion, carried out in accordance with the test presented above, it is carried out on Glucidex® 6 at 10 g/l, the product (B) at 10 g/l and product (C) tested at 10 g/l.

The results of % hydrolysis obtained over time are given in the following table.

TABLE VI

|  | 30 minutes | 60 minutes | 120 minutes |
|---|---|---|---|
| Glucidex ® 6 | 59.7 ± 9.3 | 87.9 ± 5.8 | 98.0 ± 1.8 |
| Product (B) | 20.7 ± 3.6 * | 27.7 ± 6.2 * | 33.8 ± 6.8 * |
| Glucidex ® 6 + product (B) | 30.6 ± 9.1 * | 51.0 ± 6.4 * | 63.9 ± 3.6 * |

* $p < 0.001$ with respect to Glucidex ® 6

The product (B) makes it possible to limit the hydrolysis of Glucidex® 6. At the end of intestinal perfusion, the percentage hydrolysis of Glucidex® 6 is 63.9% compared with 98.0% obtained when Glucidex® 6 is tested alone.

TABLE VII

|  | 30 minutes | 60 minutes | 120 minutes |
|---|---|---|---|
| Glucidex ® 6 | 59.7 ± 5.3 | 84.9 ± 4.4 | 100.5 ± 1.3 |
| Product (C) | 12.4 ± 9.4 * | 13.7 ± 4.0 * | 20.5 ± 7.4 * |
| Glucidex ® 6 + product (C) | 25.6 ± 8.0 * | 41.8 ± 4.5 * | 56.9 ± 5.8 * |

* $p < 0.001$ with respect to Glucidex ® 6

The product (C) makes it possible to limit the hydrolysis of Glucidex® 6. At the end of intestinal perfusion, the percentage hydrolysis of Glucidex® 6 is 56.9% compared with 100.5% obtained when Glucidex® 6 is tested alone.

The invention claimed is:

1. Hyper-branched maltodextrins having a dextrose equivalent (DE) between 8 and 15 and a weight average molecular weight (Mw) between 1700 and 3000 daltons, the maltodextrins having:
   a 1→6 glucosidic bond content between 30% and 45%;
   a soluble indigestible fiber content, determined according to AOAC method No. 2001-03, between 75% and 100%, and
   a hypoglycemic capacity, expressed according to a test A, which results:
   in vitro, in an 80% to 90% reduction in the α-amylase hydrolysis of standard maltodextrins, and
   in situ, in a 30% to 45% reduction in the intestinal digestive activity of standard maltodextrins.

2. The hyper-branched maltodextrins of claim 1, having a DE between 8 and 12 and
   a weight average molecular weight (Mw) between 2500 and 3000 daltons, characterized by:
   a 1→6 glucosidic bond content between at 30% and 35%, and
   a soluble indigestible fiber content, determined according to AOAC method No. 2001-03, between 75% and 80%.

3. The hyper-branched maltodextrins of claim 1, wherein the maltodextrins have:
   a DE between 12 and 15,
   a weight average molecular weight (Mw) between 1700 and 2500 daltons,
   a 1→6 glucosidic bond content between at 35% and 45%, and
   a soluble indigestible fiber content, determined according to AOAC method No. 2001-03, between 80% and 100%.

4. A process for preparing the hyperbranched maltodextrins of claim 1, comprising:
   (a) preparing a dehydrated acidified starch having a moisture content of less than 5%, preferably less than or equal to 4%,
   (b) treating the dehydrated acidified starch in a thin-layer reactor at a temperature between 120 and 300° C., preferably between 150 and 200° C.,
   (c) collecting, purifying and preferably concentrating the branched starch derivatives resulting from step (b),
   (d) carrying out a molecular fractionation of said branched starch derivatives so as to obtain a fraction having:
      i. an Mn between 250 and 400 g/mol,
      ii. a polydispersity index between 2 and 3,
      iii. a reducing sugar content between 20% and 30%, and
      iv. a 1~6 glucosidic bond content between 30% and 35%
   (e) optionally, treating the low-molecular-weight fraction resulting from step (d) with an amyloglucosidase,
   (f) treating the solution resulting from step (d) or (e) on a chromatographic column so as to exclude the oligomers having a degree of polymerization of 1 and 2, and
   (g) recovering hyper-branched maltodextrins resulting from step (f) having a dextrose equivalent (DE) between at least 8 and at most 15 and a weight average molecular weight (Mw) between at least 1700 and at most 3000 daltons, a 1~6 glucosidic bond content between at least 30% and at most 45%; a soluble indigestible fiber content, determined according to AOAC method No. 2001-03, between at least 75% and 100%, and
   a hypoglycemic capacity, expressed according to a test A, which results: in vitro, in an 80% to 90% reduction in the α-amylase hydrolysis of standard maltodextrins, and in situ, in a 30% to 45% reduction in the intestinal digestive activity of standard maltodextrins.

5. A food product or pharmaceutical product comprising the hyper-branched maltodextrins of claim 1.

6. A method for preparing food product or pharmaceutical product, comprising combining the hyper-branched maltodextrins of claim 1 with a food product or pharmaceutical product composition.

7. A method for preparing food product or pharmaceutical product, comprising combining the hyper-branched maltodextrins as obtained according to the process of claim 4 with a food product or pharmaceutical product composition.

8. The hyper-branched maltodextrins of claim 1, wherein the maltodextrins have a number-average molecular weight (Mn) of between 865 g/mol to 1595 g/mol.

* * * * *